United States Patent [19]

Cerny et al.

[11] Patent Number: 4,786,286
[45] Date of Patent: Nov. 22, 1988

[54] FLUID TRANSFER SYSTEM

[75] Inventors: David E. Cerny, Crystal Lake; David V. Bacehowski, Wildwood, both of Ill.

[73] Assignee: Baxter Travenol Laboratories, Inc., Deerfield, Ill.

[21] Appl. No.: 868,202

[22] Filed: Mar. 23, 1986

Related U.S. Application Data

[63] Continuation of Ser. No. 705,572, Feb. 26, 1985, abandoned.

[51] Int. Cl.⁴ .............................................. A61B 19/00
[52] U.S. Cl. .................... 604/406; 604/284; 604/326; 604/403; 604/905; 128/767
[58] Field of Search ........................ 604/326, 408–416, 604/283, 284, 905, 322, 323, 403, 406; 128/762, 767; 210/782, 927; 422/44, 101; 494/21

[56] References Cited

U.S. PATENT DOCUMENTS

| | | | |
|---|---|---|---|
| 2,702,034 | 2/1955 | Walter . | |
| 3,064,647 | 11/1962 | Earl . | |
| 3,327,709 | 6/1967 | Nehring et al. | 604/409 |
| 3,467,095 | 9/1969 | Ross | 604/408 |
| 3,874,384 | 4/1975 | Deindoerfer et al. | 604/408 |
| 3,916,892 | 11/1975 | Latham, Jr. | 604/326 |
| 3,986,506 | 10/1976 | Garber et al. . | |
| 3,986,508 | 10/1976 | Barrington . | |
| 4,004,586 | 1/1977 | Christensen et al. | 604/413 |
| 4,022,256 | 5/1977 | Berkman et al. . | |
| 4,058,363 | 11/1977 | Silbert | 604/403 |
| 4,112,989 | 8/1978 | Grode et al. | 604/262 |
| 4,157,723 | 6/1979 | Granzow et al. . | |
| 4,223,675 | 9/1980 | Williams . | |
| 4,332,122 | 6/1982 | Williams | 604/408 |
| 4,356,394 | 10/1982 | Cobean et al. . | |
| 4,386,622 | 6/1983 | Munsch | 604/408 |
| 4,611,643 | 9/1986 | Beebe et al. . | |

FOREIGN PATENT DOCUMENTS 2142240 1/1985 United Kingdom ................ 604/408

Primary Examiner—John D. Yasko
Assistant Examiner—Mario Costantino
Attorney, Agent, or Firm—Paul C. Flattery; Paul M. Vargo; Bradford R. L. Price

[57] ABSTRACT

A fluid collection system includes an input unit having a hollow needle coupled through a section of flexible conduit to an anticoagulant reservoir which is in turn coupled via a second section of hollow conduit to a first sterile connector. A collection container, which can be a dry, flexible, plastic bag, is coupled by a plastic conduit to second and third sterile connectors. The first and second connectors can be joined together and sealed to form a sterile system. A transfer container includes a flexible plastic container coupled via a hollow plastic conduit to a fourth sterile connector. The fourth sterile connector is joinable with the third sterile connector to form a sterile two container system. Fluids collected in the primary container can then be transferred to the secondary container.

5 Claims, 3 Drawing Sheets

FLUID TRANSFER SYSTEM

This application is a continuation of application Ser. No. 705,572, filed Feb. 26, 1985, now abandoned.

BACKGROUND OF THE INVENTION

The present invention pertains to fluid collection systems. More particularly the present invention pertains to apparatus for use in collection of blood.

The equipment used today in the collection of blood is usually formed as a series of two or three integrally connected, sterile, plastic bags with a hollow needle affixed to the end of a conduit which is in turn coupled to one of the bags. This collection set may be sterilized during the manufacturing process so as to form a sterile, closed, system for the collection and later processing of blood. Collection sets formed of plastic have the advantage of being disposable and also the advantage of permitting the collection, storage, and transfer of the blood within a single sterile processing system. The two or three interconnected containers can be filled with blood components such as plasma and/or platelets which are separated from the red blood cells after the initial collection.

The processing that any given unit of blood is to receive is often not known in advance. As a result, it is necessary for collection agencies to stock two-bag and three-bag collection systems. This results in increased overhead and inventory costs. At times this also results in expensive three-bag sets being used where a two-bag set might provide the desired capacity and processing capability.

Because of the need to provide a complete sealed sterile system in which the blood is collected and through which it is transferred during the processing phases, no alternate systems have been available on a commercial basis which were of a non-integrally formed variety. A set disclosed in U.S. Pat. No. 4,223,675 issued Sept. 23, 1980 and assigned to Baxter Travenol Laboratories, Inc. provides a container that contains an anticoagulant liquid. This container can in turn be coupled by a sterile connector to a preformed three-bag collection set. The set of the above noted patent includes a needle for insertion into the body from which the blood is to be drawn or collected. The needle is coupled by a conduit to a primary collection container. The conduit coupling the needle to the primary collection container is integrally attached to that container.

A sterile connector of the type disclosed in the above-noted patent is disclosed in more detail in U.S. Pat. No. 4,157,723, entitled "Method of Forming a Connection Between Two Sealed Conduits Using Radiant Energy" which issued June 12, 1979 and which was assigned to Baxter Travenol Laboratories, Inc. Another sterile connector is disclosed in U.S. Pat. No. 4,022,256 entitled "Aseptic-Fluid Transfer System" which issued May 10, 1977.

SUMMARY OF THE INVENTION

In accordance with the present invention, a fluid transfer set is provided which includes a hollow needle for insertion into a corporal body for collection of a selected fluid, such as blood, a hollow conduit affixed to a selected end of a needle, sealed means for storing a selected additive mixable with at least part of the collected fluid and first means for forming a sterile connection also coupled to the conduit.

Further, in accordance with the invention, second means for forming a sterile connection can be provided which are joinable with the first means for forming a sterile connection. A second hollow conduit can be coupled to the second sterile connection means and in turn coupled to dry means for receiving the collected fluid. Further, in accordance with the invention, the fluid collection system can include third means for forming a sterile connection also coupled to the second conduit and to the collection means. Fourth means for forming a sterile connection can be provided, joinable to the third sterile connection means. Second means for receiving at least part of the collected fluid can be coupled to the fourth sterile connection means.

DETAILED DESCRIPTION OF THE PREFERRED EMBODIMENT

Figure 1:
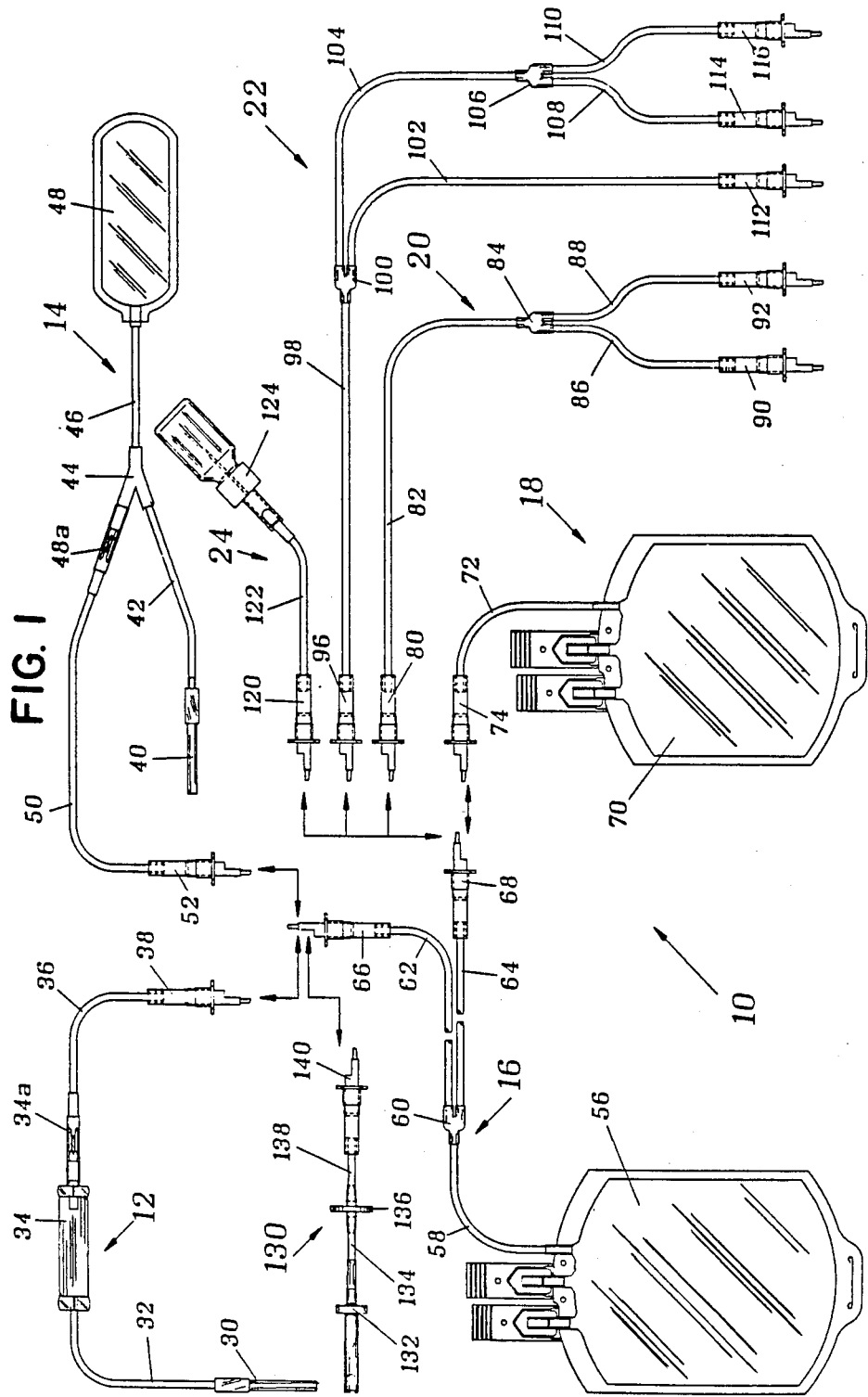
FIG. 1 illustrates in schematic diagram form an embodiment of the present invention.

With respect to the Figures, FIG. 1 illustrates a fluid transfer system 10 which includes a fluid donor unit 12, an alternate fluid donor unit 14, a primary collector unit 16 and a secondary or transfer unit 18. In addition, the system 10 can also include interface units 20 and 22 an also a vial adaptor unit 24.

More particularly, the donor unit 12 includes a hollow needle 30, shown in a protective cover, which is intended to be inserted into a corporal body from which the fluid, possibly blood, is to be collected. The fluid which is collected flows through the hollow needle 30, through a first part of a flexible plastic conduit 32 through an anticoagulant reservoir 34, through a second part of the hollow plastic conduit 36 and then out through a sterile connector 38.

The anticoagulant reservoir 34 includes an in-line frangible cannula 34a which is manually broken prior to collecting the fluid, such as blood. The anticoagulant liquid drains through the section of conduit 36 and the connector 38 into the primary collector unit 16 prior to the fluid being collected through the needle 30.

The sterile connector 38 is of a type which is disclosed in U.S. Pat. No. 4,611,643, filed Nov. 21, 1983, entitled "Interlocking Fluid Transfer Device and Resulting Assembly" and assigned to the assignee of the present application. The disclosure of that application is hereby incorporated by reference herein. The sterile connector 38 could also be of the type disclosed in the above noted U.S. Pat. No. 4,022,256.

As an alternate to the collector unit 12, the collector unit 14 may be utilized. The collector unit 14 includes a needle 40, shown within a protective cover, corresponding to the covered needle 30, which is coupled via a flexible hollow conduit 42 to a three-way fluid connector 44. The connector 44 is coupled by a hollow plastic conduit 46 to an alternate anticoagulant reservoir 48. The reservoir 48 can be formed of a flexible plastic material. The reservoir 48 includes an internal, in line, frangible cannula 48a which can be manually broken at an appropriate time in the processing step. The three-way fluid connector 44 is also coupled via a third flexible conduit 50 to a sterile connector 52 of the type disclosed in the above incorporated patent application.

The primary unit 16 includes a dry, empty, flexible plastic receptacle or collection container 56 having a capacity on the order of 600 ml. The container 56 is coupled by a flexible plastic conduit 58 through a three-way fluid connector 60 to a pair of flexible plastic conduits 62 and 64. The conduit 62 is coupled to a sterile connector 66. The conduit 64 is coupled to a sterile connector 68. The container 56 can be a flexible plastic bag. In addition to being used as a primary fluid collection container in combination with the donor units 12 or 14, the dry, empty container 56 can be used as a large volume secondary fluid transfer container. This flexibility is achieved by locating the anticoagulant material in the separate, sealed reservoirs 34 or 48. This flexibility makes the system 10 especially suited and cost effective for a wide variety of applications that may require transfer of a unit of fluid without adding anticoagulant material.

Under normal blood collection practices, the collection unit 12 would be combined with the primary fluid collection unit 16 by joining the sterile connector 38 with the sterile connector 66. The connectors 38 and 66 are then fused together as disclosed in the above incorporated patent application to form a sterile connection. An apparatus for fusing the connectors, such as 38 and 66, together is disclosed in U.S. Pat. No. 4,356,394 entitled "Apparatus for Applying Radiant Beam" which issued Oct. 26, 1982 and was assigned to Baxter Travenol Laboratories, Inc. The disclosure of that patent is hereby incorporated by reference herein. If connectors of the type disclosed in the above noted U.S. Pat. No. 4,022,256 are used, as the connectors 38 and 66 for example, then the fusing or joining is brought about by the use of heat as disclosed and taught in that patent.

After the selected connectors have been fused or joined together, the fluid would flow through the conduit 32, through the previously emptied anticoagulant reservoir 34, through conduit 36, through sealed sterile connectors 38, 66, the conduits 62 and 58 and into the primary container 56. The collector unit 14 could also be used in the same way with the primary collection unit 16.

The transfer unit 18 includes a flexible container 70 which is coupled by a flexible conduit 72 to a sterile connector 74. The connector 74 corresponds to the type of sterile connector disclosed in the above noted patent application. The container 70 could be formed with a volume on the order of 300 ml as a dry, empty, sterile transfer container.

Under normal blood collection procedures, once the blood has been accumulated in the primary container 56, it can be centrifuged to separate the plasma from the red blood cells, as is known in the art. The plasma can be expressed from the container 56 through the sealed connectors 68, 74 into the secondary or transfer container 70.

For the purpose of coupling the input unit 12 or the input unit 14 to alternate types of containers or devices, the dual lead interface unit 20 may be used. The unit 20 includes a sterile connector 80 attached to an end of a conduit 82. The conduit 82 is in turn coupled to a three-way fluid connector 84. The fluid connector 84 is coupled to conduits 86 and 88. Conduit 86 has a sterile connector 90 coupled thereto. Conduit 88 has a sterile connector 92 coupled thereto. The interface unit 20, via the sterile connector 80, can be coupled to, for example, the sterile connector 68 or the connector 38. The sterile connectors 90, 92 can be in turn joined to other sterile connectors such as the connectors 66 or 74 for example.

As an alternate to the interface unit 20, the triple lead interface unit 22 may be used. The interface unit 22 includes a sterile connector 96 which is coupled by a flexible hollow conduit 98 to a first three-way connector 100. The connector 100 is coupled to hollow flexible conduits 102 and 104. Conduit 104 is in turn connected to a three-way fluid connector 106. The fluid connector 106 is connected to hollow flexible conduits 108 and 110. The conduit 102 terminates in a sterile connector 112. The conduit 108 terminates in a sterile connector 114. The conduit 110 terminates in a sterile connector 116. Either the interface unit 20 or the interface unit 22 can be used with the input units 12 or 14 or the collector units 16 or 18. The interface units 20 or 22 may also be used with other types of collection or transfer containers or other types of apparatus. The interface units 20, 22 only require that connectors be affixed to the containers or apparatus that are compatible with and joinable to the connectors, 90,92, 112,114 or 116.

A vial adaptor unit 24 can also be used with the primary or secondary collection units 16 and 18. The vial adaptor unit 24 provides a sterile, closed fluid flow path through which a quantity of collected volume can be transported into an arbitrary, removable container. The vial adaptor unit 24 includes a sterile connector 120 coupled by a flexible conduit 122 to a removable reservoir or a vial 124. The reservoir or vial 124 conventionally includes a rubber stopper and can include an internal needle which extends through the rubber stopper to provide for a flow of blood from the container 56 to the vial 124.

A sterilizing filter connection set 130 is also usable in combination with the elements of the system 10. The set 130 includes a plastic needle or spike 132 of a conventional variety affixed to an end of a hollow plastic conduit 134. At the other end of the conduit 134 is a 22 Micron sterilizing filter 136 of a conventional variety. The output side of the filter 136 is coupled to a hollow conduit 138. The conduit 138 is in turn connected or coupled to a sterile connector 140. The sterile connector 140 is joinable with the other sterile connectors such as the connectors 38, 52, 66, 74, 80, 96, 112-116 or 120 of the system 10.

The set 130 can be used to couple an arbitrary bag of fluid or drugs to the primary container 56 or the secondary container 70. The needle or spike 132 can be used, as is conventional to puncture the bag containing the fluid or drugs to be added. The fluid or drugs to be added flow through the conduit 134, are sterilized by the filter 136, flow through the conduit 138 and out through the connector 140 into other elements of the system 10 to which the connector 140 is joined. The set 130 provides for introduction of an unsterilized fluids or drugs through the needle 132, via the filter 136, in an essentially sterile form, into elements of the system 10.

In one form of operation, an operator would select one of the donor units 12 or 14, the primary collector unit 16, one or two secondary collector units 18 and the interface unit 20. The appropriate sterile connectors such as 38, 66; and 68,74 for a two container set would be manually joined together. The sterile connectors would then be sealed together using radiant energy or heat as disclosed in the above incorporated patent application or U.S. Pat. No. 4,022,256 respectively, to form a sealed, sterile system. The fluid or blood would in a standard fashion be collected into the primary container 56. The components would then be separated in a known fashion and transferred into the secondary containers, such as the secondary container 70 for distribution and use.

Figure 2:
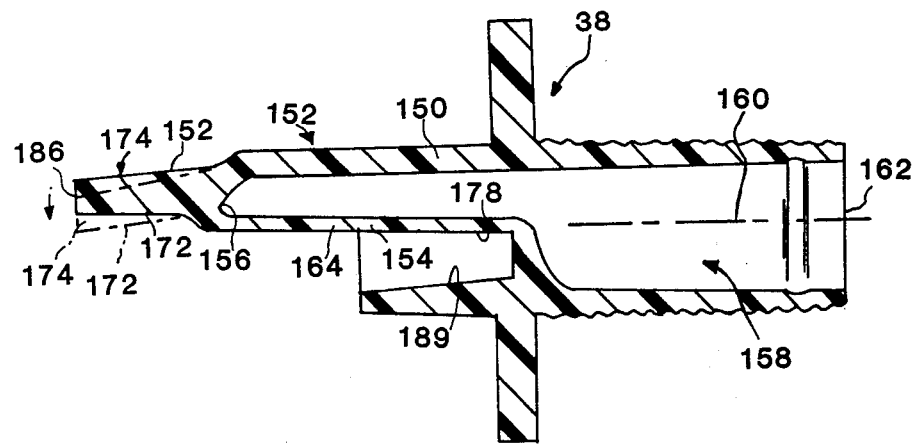
FIG. 2 is a side sectional view of an exemplary sterile connector usable in the embodiment of the present invention.

With respect to the sterile connectors, such as the connectors 38, 52 or 66 of FIG. 1, FIG. 2 illustrates in further detail the structure thereof as taught by the above noted, incorporated patent application.

As disclosed in FIG. 2, a sidewall 150 of a tubular body 152 of each connector such as connectors 38, 52 or 66 includes a generally planar surface portion 154. The surface portion 154 extends rearwardly from a closed end 156 of a bore 158 in a plane which is generally parallel to axis 160 of the bore 158. An opening 162 at the rear of the exemplary connector 38 permits fluid to flow through the connector to or from an attached flexible conduit such as the conduit 36 attached to the connector 38.

While various configurations can be used, due to the particular position of the planar surface portion 154 in the illustrated embodiment, the internal dimension of the bore 158 adjacent to its closed end 156 is about one-half the internal dimension of the bore 158 adjacent its open end 162.

The planar surface portion 154 includes a region 164 which, when heated, is meltable to form an opening communicating with the bore 158. Fluid can be conducted through this formed opening. The meltable region 164 is generally centered along a centerline axis 166 of the planar surface portion 154 (see FIG. 3). The meltable region 164 is also preferably positioned in close proximity to the closed end 156 of the bore 158 to minimize the size of the area between the formed opening and the closed bore end 156, in which fluid can become entrapped.

The region 164 preferably melts only at temperatures which result in the destruction of bacterial contaminants, i.e., over 200° C. In this preferred arrangement, the region 164 can be opened only in connection with an active sterilization step which serves to sterilize the regions adjacent to the fluid path as the fluid path is formed.

When two connectors such as 38 and 66 are joined, the meltable regions 164 of the two devices 38 and 66 are aligned and placed in intimate facing contact. When jointly heated, both of the regions 164 melt, fusing the two devices 38 and 66 together. A fluid path 170 (see FIG. 5) is also opened between the two connectors 38 and 66, and thus between the attached conduits 36 and 62.

As best shown in FIG. 2, while a planar tab surface 172 is generally parallel to the planar body surface portion 154, the two surfaces 172 and 154 are themselves not coplanar. Instead, the planar tab surface 172 is offset in the direction of the bore 158 away from the planar body surface portion 154.

Figure 3:
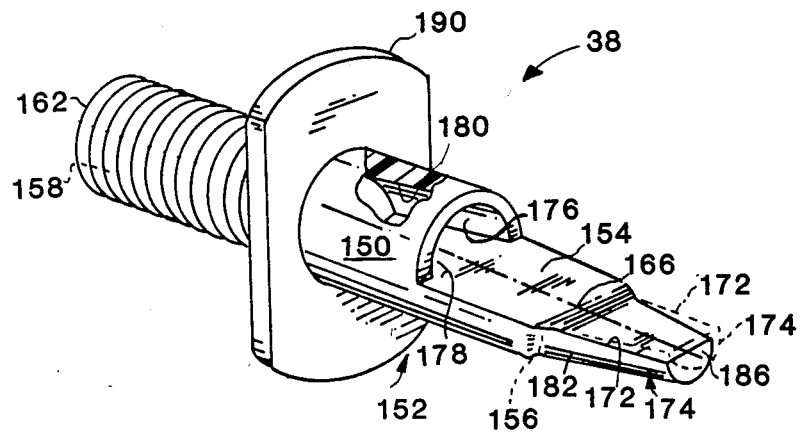
FIG. 3 is a perspective view, partly broken away, of the sterile connector of FIG. 2.

As shown by arrows and in phantom lines in FIGS. 2 and 3, a tab 174 of each connector such as 38 and 66 is resiliently deformable relative to the body 152 out of its normal position in response to external force in a direction transverse of the axis 166.

The interior configuration of a slot 176, like the exterior configuration of the tab 174, constitutes a cone which has been truncated in two planes. The slot 176 thus includes a generally planar surface 178, the axis 166 of which is centered along the planar surface 154 (see Figure 3), as well as an accurate surface 180, which extends radially outwardly from the axis 166 and which tapers toward the axis 166 in a direction toward the open end 162 of the bore 158. The slope and taper of the accurated slot surface 180 correspond with the slope and taper of an external accurate tab surface 182.

The tab 174 of the connector 38 will thus uniquely mate with the slot 176 of the connector 66, and vice versa, but only when the centerline 166 of the tab 174 and slot 176 are aligned. When the centerlines 166 do not align, the tab 174 and slot 176 do not mate. Instead, a planar end surface 186 of the tab 174 abuts against the entrance of the slot 176.

Figure 4:
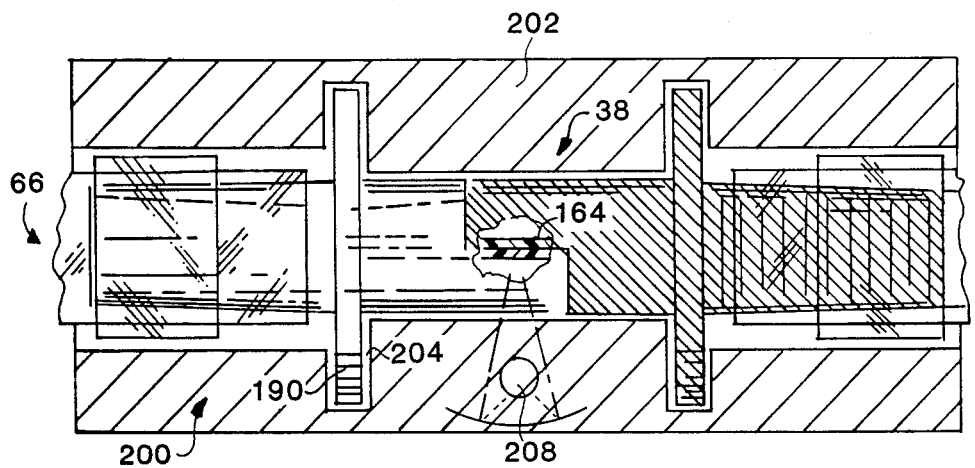
FIG. 4 is a view, partly broken away and in section, of two sterile connectors joined together in an apparatus for applying radiant energy thereto.

As shown in FIG. 4, a device 200 can be used to generate the melting energy. The device 200 includes a base 202 having a pair of spaced apart holders 204. The holders 204 jointly receive a collar 190, but only when the collars 190 are spaced apart the same distance as the holders 204. By purposeful design, when the meltable regions 164 are not in the desired registration, the collars 190 are spaced either farther or closer apart than the holders 204. Thus, when the meltable regions 164 are not in the desired registration, the connectors, such as the connectors 38 and 66, cannot be physically mounted in the device 200.

The type of energy employed to melt the region 164 of the planar surface 154 can vary. For example, thermal conduction can be used as disclosed in the above-noted U.S. Pat. No. 4,022,256. In this arrangement (not shown), the energy source constitutes a heat plate or the like in contact with the body 152 of at least one of the connectors 38 or 66. The body 152 of the connector 38 would, in this embodiment, be made of a thermosetting or high melt point material which would conduct heat energy from the source to the engaged meltable regions 164. The meltable regions 164 would be made of a material having a lower melting g temperature than the body 152. The conducted energy would thus melt only the region 164, not the surrounding body 152.

In the illustrated and preferred embodiment, however, thermal radiation is used to heat the meltable region 164. In this arrangement, the body 152 of each of the connectors 38 and 66 is made entirely of a thermoplastic material which can be molded by conventional means. The meltable region 64 of at least one of the connectors 38 and 66 includes a radiant energy absorbing material which is intermixed with or applied upon the surface of the thermoplastic body material. By applying a sufficient amount of radiant energy, the radiant energy absorbing region 164 is heated until melting occurs. An opening is formed in the region 164. Fluid communication is thereby opened with the associated conduit via the region 170.

As used herein, the term 'radiant energy' broadly refers to energy which is in the form of electromagnetic waves, such as radio waves, infrared waves, visible light, ultraviolet waves, x-rays and the like. Because the transfer of radiant energy requires no intervening medium, the transfer can be faster and more efficient than in conductive or convected heat transfer, both of which require an intervening medium.

Because, in the illustrated and preferred embodiment, thermal radiation is the means employed to heat the overlying regions 164, the body 152 of at least one of the connectors 38 or 66 must be capable of transmitting the radiant energy to the meltable regions 164 of the connector.

Figure 5:
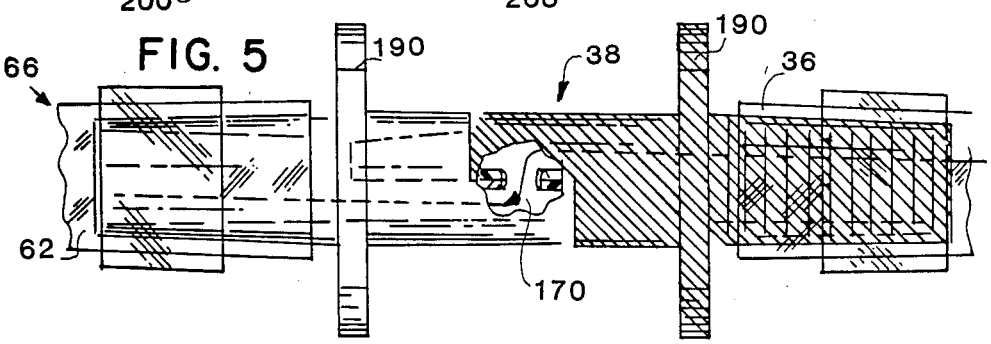
FIG. 5 is a planar view partly broken away, of two exemplary sterile connectors that have been fused together.

In the illustrated embodiment, the thermoplastic body 152 of the one connector 38 can be made uniformly absorbent (i.e., opaque to) the applied radiant energy (see FIGS. 4 and 5). The thermoplastic body 152 of the other connector 66 can be made of a material which absorbs the applied radiant energy in lesser amounts than the opaque material of the connector 38. Preferably, the entire body 152 of this connector 66 is relatively nonabsorbent of (i.e., transparent to) the particular type of radiant energy which will be applied.

In this arrangement, as shown in FIG. 4, after the connectors 38 and 66 are fitted into the device 200, radiant energy is applied from a source 208 to the assembly 38 and 66 through the transparent body 152 of the device 66 and focused upon the meltable regions 164. The source 208 comprises an incandescent quartz lamp which has a tungsten filament operating at about 3150° K. This lamp emits radiant energy which lies in a continuous band encompassing mostly infrared and visible energy, although some ultraviolet radiation is included.

The transparent body 152 is itself not heated to any great extent by the radiant energy. However, in response to the applied thermal radiation, the meltable region 164 of the opaque connector 38 is heated to a temperature sufficient to melt the opaque region 164.

Because, in accordance with the invention, the regions 164 are held in intimate contact, the thermoplastic (i.e., meltable) region 164 of the transparent connector 66 conducts heat from the opaque region 164 in sufficient quantities to also melt. As a result, the regions 164 jointly melt and fuse together.

In the process of melting, the regions 164 form the opening 170 (see FIG. 5) which establishes through the coupled connectors 38 and 66 a fluid path which is hermetically sealed about its periphery.

Because, in accordance with the invention, the coupling means 176 assures the proper alignment between the meltable regions 164, the formed opening is uniform with respect to each region 164, lying along the centerline 166 of each planar surface portion 154.

The particular materials selected for the connectors 38 and 66 depend largely upon the type of radiant energy which is to be applied.

In the illustrated embodiment, in which infrared and visible light are used, the connectors, such as the connectors 38 and 66, can be made of a material fabricated from poly(4-methyl-1-pentene), which is sold under the trademark TPX by Mitsui Chemical Company. This thermoplastic material has a crystalline melting point of approximately 235° C. and is further discussed in Boggs et al U.S. Pat. 4,325,417.

The opaque connector 38 includes, intermixed with the TPX material, a charcoal filler. It thus absorbs radiant energy in the infrared and visible light band. The TPX material of the transparent connector 66 is free of the filler and is relatively transparent to (i.e., generally nonabsorbant of) this band of radiant energy.

Figure 6:
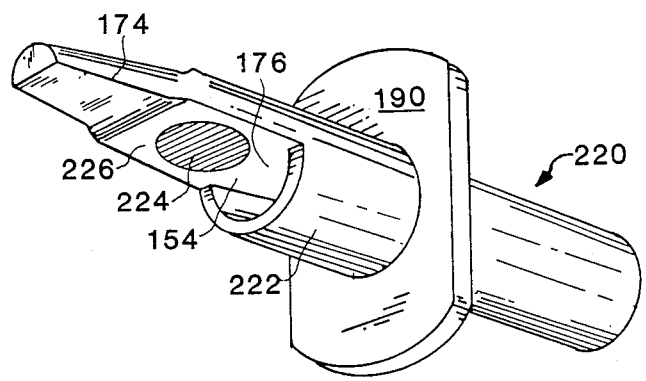
FIG. 6 is a view in perspective of another exemplary sterile connector.

Alternately, as shown in FIG. 6, instead of using the opaque connector such as shown in FIGS. 2 or 3, a connector 220 can be used. The connector 220 has a body 222 which is uniformly transparent to the passage of the applied radiant energy, like the body of the connector 66 as just described. However, in this arrangement, a radiant energy absorbing material 224 is affixed on the external surface of a meltable region 226, for example by hot stamping, printing, gluing, and the like. As before described, thermal radiation will heat the material 224 and cause the region 226 to melt.

Two of the connectors 220 can be coupled together to form an assembly with the applied meltable regions 224 position in intimate facing contact. The radiant energy generating apparatus 200 can then be used to fuse the two connectors together.

The size of the mating connectors, such as the connectors 38 and 66, can vary according to the intended field of use. In a representative embodiment, the overall length of each connector such as 38 or 66 is approximately 1.4 inches, and the maximum outside diameter, exclusive of the collar 190, is about 0.3 inch. In this arrangement, the tab 174 extends about 0.261 inch outwardly from the closed end 156 of the bore 158. Both the tab 174 and the slot 176 have an accurate surface, respectively 182 and 189, with an approximate slope of 5°. The accurate surface 182 of the tab 174 has an arc of approximately 0.092 inch radius adjacent to the planar end surface 186. The planar surface 178 of the slot 176 has an arc of approximately 0.112 inch radius at the entrance of the slot 176. The planar surface 172 of the tab 174 is offset from the planar surface portion 154 of the body 152 by about 0.003 inch. In this arrangement, an approximately 0.0012 inch interference fit develops between the tab 174 and slot 176 when the meltable regions are in proper registration.

It will be understood that broader aspects of the invention include the use of disposable containers or interface units having alternate forms of sterile connectors than are disclosed herein. It will also be understood that the use of all forms of heat or radiant energy to seal two sterile connectors together come within the scope of the present invention. Further, it will be understood that the exact shape or size of the sterile connectors are not limitations to the present invention. The anticoagulants, previously referred to in connection with the reservoirs 34 and 48, could be dry anticoagulants rather than liquid anticoagulants without departing from the spirit and scope of the invention. It will also be understood that while in the exemplary embodiment illustrated in FIG. 1, the primary container 56 has been described as a dry, empty, container, it is within the scope of the invention for the primary container to have been pre-loaded with fluids or drugs to be mixed with the additive in the container 34, after the frangible 34a has been broken, and the primary fluid being collected. It is also within the scope of the invention to pre-load the secondary containers, such as the container 70, with fluids or drugs to be added to the components or portions of the collected fluids which have been expressed into those containers. In addition, while the present embodiment of the invention is suitable for the collection and processing of blood, it will be understood that the invention is usable with the collection or processing of other bodily fluids without limitation.

We claim:

1. A modular, sealed fluid transfer system assemblable into a selected configuration in response to applied radiant energy comprising:
   a first flexible container module with integrally attached first and second tubing members, each said tubing member having a free end, first and second shaped, non-piercing plastic connector means, each said connector means coupled to a respective one of said first and said second free ends;
   a filter module with a tubular conduit having first and second ends, a piercing needle in fluid flow communication with said first end, a fluid filter element carried by said conduit and a third, shaped, non-piercing plastic connector means coupled to said second end;
   a vial module including a fluid containing vial and a fluid flow conduit with first and second ends, said vial coupled to said first end of said conduit, said second end carrying fourth shaped, non-piercing plastic connector means;
   said first and said third connector means slidably engageable with one another so as to form a permanent, sealed fluid flow path between said connector means in response to applied radiant energy and
   said second and said fourth connector means slidably engageable with one another so as to form a permanent, sealed fluid flow path between said connector means in response to applied radiant energy.

2. A modular sealed fluid transfer system as in claim 1 with each said connector means including a planar connection region such that as respective connector members engage one another, respective of said planar connection regions are juxtaposed with one another.

3. A modular sealed fluid transfer system as in claim 1 with each said connector means substantially identical to each other of said connector means.

4. A modular, sealed fluid transfer system assemblable into a selected configuration in response to applied radiant energy comprising:
   a first flexible container module with integrally attached first and second tubing members, each said tubing member having a free end, first and second shaped, non-piercing plastic connector means, each said connector means coupled to a respective one of said first and said second free ends;
   a fluid inflow module selected from a class including
     (a) a filter module with a tubular conduit having first and second ends, a piercing needle in fluid flow communication with said first end, a fluid filter element carried by said conduit and a third, shaped, non-piercing plastic connector means coupled to said second end; and
     (b) an anticoagulant containing module with tubular conduit flow means having first and second ends, a piercing needle in fluid flow communication with said first end, an anticoagulanat container carried by said conduit flow means, and shaped non-piercing plastic connector means coupled to said second end;
   a fluid outflow module selected from a class including
     (c) a vial module including a fluid containing vial and a fluid flow conduit with first and second ends, said vial coupled to said first end of said conduit, said second end carrying fourth shaped, non-piercing plastic connector means;
     (d) multibranch transfer conduit flow means having an initial conduit member with first and second ends, as well as secondary and tertiary conduit members each with first and second ends, said initial conduit member coupled to said secondary and tertiary conduit members at respective of said second ends, shaped non-piercing plastic connector means coupled to each said first end; and
     (e) a fluid receiving container module carrying non-piercing plastic connector means;
   said first connector means slidably engageable with connector means associated with said fluid inflow module so as to form a sealed fluid flow path between said connector means in response to applied radiant energy; and
   said second connector means slidably engageable with connector means associated with said fluid outflow module so as to form a sealed fluid flow path between said connector means in response to applied radiant energy.

5. A modular sealed fluid transfer system as in claim 4 with each said connector means including a planar connection region such that as respective connector members engage one another, respective of said planar connection regions are juxtaposed with one another.

* * * * *